United States Patent [19]

Shemwell et al.

[11] Patent Number: 6,095,974

[45] Date of Patent: *Aug. 1, 2000

[54] DISPOSABLE FIBER OPTIC PROBE

[75] Inventors: David M. Shemwell, Seattle, Wash.; George R. Ryan, Level Green, Pa.

[73] Assignee: Respironics, Inc., Pittsburgh, Pa.

[*] Notice: This patent is subject to a terminal disclaimer.

[21] Appl. No.: 09/209,380

[22] Filed: Dec. 10, 1998

Related U.S. Application Data

[63] Continuation of application No. 08/683,800, Jul. 18, 1996, abandoned, which is a continuation-in-part of application No. 08/505,035, Jul. 21, 1995, abandoned.

[51] Int. Cl.$^7$ ..................................................... A61B 5/00
[52] U.S. Cl. ........................... 600/310; 600/322; 600/323
[58] Field of Search ........................... 600/310, 322–324, 600/326, 340, 473, 476

[56] References Cited

U.S. PATENT DOCUMENTS

| | | |
|---|---|---|
| 3,799,672 | 3/1974 | Vurek . |
| 3,847,483 | 11/1974 | Shaw et al. . |
| 3,951,514 | 4/1976 | Medina, Jr. . |
| 3,998,550 | 12/1976 | Konishi et al. . |
| 4,167,331 | 9/1979 | Nielsen . |
| 4,597,631 | 7/1986 | Flores . |
| 4,621,642 | 11/1986 | New, Jr. et al. . |
| 4,763,976 | 8/1988 | Nolan et al. . |
| 4,773,442 | 9/1988 | Isaacson et al. . |
| 4,819,752 | 4/1989 | Zelin . |
| 4,824,242 | 4/1989 | Frick et al. . |
| 4,848,901 | 7/1989 | Hood, Jr. . |
| 4,883,353 | 11/1989 | Hausman et al. . |
| 4,890,619 | 1/1990 | Hatschek . |
| 4,925,267 | 5/1990 | Plummer et al. . |
| 5,039,491 | 8/1991 | Saaski et al. . |
| 5,090,410 | 2/1992 | Saper et al. . |
| 5,109,452 | 4/1992 | Selvin et al. . |
| 5,127,071 | 6/1992 | Go . |
| 5,209,230 | 5/1993 | Swedlow et al. . |

(List continued on next page.)

FOREIGN PATENT DOCUMENTS

745348A1  12/1996  European Pat. Off. .

OTHER PUBLICATIONS

Technical Staff of CSELT, *Optical Fibre Communication*, 1980, pp. 13–17.

*Primary Examiner*—Linda C. M. Dvorak
*Assistant Examiner*—Bryan K. Yarnell
*Attorney, Agent, or Firm*—Reed Smith Shaw & McClay, LLP

[57] ABSTRACT

An apparatus for transferring two frequencies of electromagnetic energy to and from a portion of a living body for the purpose of blood oxygen saturation measurements. The two frequencies of electromagnetic energy are transferred to the portion of the living body through a single optical fiber cable (which could be a bundle) to a coupler and then through a short section of optical cable to an optical element adjacent to the portion of the living body. After the two frequencies of electromagnetic energy are transmitted through the portion of the living body they are received by another optical element and transported away from the portion of the living body to a coupler through a short section of optical cable where they may be converted to electrical signals. Alternatively, the two frequencies of electromagnetic energy are carried away from the coupler. The signals from the coupler (whether they are electromagnetic signals or electrical signals) are directed to a measurement instrument, which through an adapter may be a conventional measurement instrument known in the prior art or a measurement instrument specifically designed for use with the signals produced at the coupler. The two short sections of optical cable and the two optical elements adjacent to the portion of the living body and the coupler are combined to form a disposable probe. Alternatively, the disposable probe can include a transducer to convert the transmitted optical energy to electrical signals.

12 Claims, 7 Drawing Sheets

U.S. PATENT DOCUMENTS

| | | |
|---|---|---|
| 5,279,295 | 1/1994 | Martens et al. . |
| 5,285,783 | 2/1994 | Secker . |
| 5,285,784 | 2/1994 | Seeker . |
| 5,309,537 | 5/1994 | Chun et al. . |
| 5,339,810 | 8/1994 | Ivers et al. . |
| 5,355,882 | 10/1994 | Ukawa et al. . |
| 5,385,143 | 1/1995 | Aoyagi . |
| 5,411,023 | 5/1995 | Morris et al. . |
| 5,413,100 | 5/1995 | Barthelemy et al. . |

DISPOSABLE FIBER OPTIC PROBE

This application is a continuation of application Ser. No. 08/683,800, filed on Jul. 18, 1996, now abandoned, which is a continuation-in-part of application Ser. No. 08/505,035, filed on Jul. 21, 1995, now abandoned.

DESCRIPTION

1. Technical Field

The present invention relates to methods and apparatus for exposing a living body to electromagnetic energy, and more particularly, to methods and apparatus for exposing a living body to laser light energy via multifiber optical cables and for receiving information in the laser light energy after passage of the laser light energy through the living body.

2. Background of the Invention

It is possible to determine the oxygen saturation level in the blood stream of a living being by comparing the absorption of two different wavelengths of light, typically red and infrared, after the light has transited a blood saturated portion of the body. In practice on humans, the section of the body illuminated is usually a finger, earlobe, hand, foot or the nose. This task is typically accomplished by using two light emitting diodes, one red and one infrared. The diodes are placed in contact with the skin, and photodiodes record the respective amounts of light from each source that is transmitted.

There are a number of problems associated with this current art method. It is important that the wavelengths of the light be carefully controlled so that the amount of the absorbed portion of the incident light is calibrated, and the data is therefore accurate. In the case of light emitting diodes (LEDs) there is a wide variability in wavelength intrinsic to the mass production process. The actual wavelength of light produced also depends on the applied voltage. It is therefore possible to establish the wavelength of the light produced by an LED for this method by matching the wavelength variability of the individual LED with a specific applied voltage. The specific voltage applied to the LED may be established by using a series of resistors in conjunction with a known constant voltage source. One problem with this approach is that each individual LED must be treated. The LED must be customized by matching it with a specific set of resistors. This process is time consuming and expensive. Typically without this customization this technique requires extensive calibration of the calibration equipment and of the sensor to the equipment. This results in a long term problem of sensor interchangeability from unit to unit and between pieces of competitive equipment.

Another problem associated with current art is that the LED is typically in direct contact with the skin of the patient to be treated. LEDs are typically 20 to 30 percent efficient; therefore 70 to 80 percent of the applied electrical power is dissipated in the form of heat. In some cases this excess heat has been known to burn the patient, particularly when current art sensors are used for infant or neonatal care.

The two LEDs which produce the two wavelengths necessary for the measurement are not co-located in the current art. This means that the pathway of the two different forms of light is different and when the patient moves about, it is possible for the pathways to vary and to vary differently. This contributes to an effect known in the community as "motion artifact." The accuracy of the present method depends on the absorption varying only due to differential absorption in the blood. Therefore, varying pathways can lead to absorption variations which do not depend on the blood and can, accordingly, degrade the blood oxygen measurement. A major problem with the current technology is the resulting false alarms.

The wavelength range of an LED light source, while narrow in wavelength spread compared to an incandescent source, is still very broad. It is therefore difficult for LED-based measurement systems to filter out other lights (such as room lights) which are part of the environment rather than the desired light source. In the current art, room light can degrade the measurement.

Two additional problems with the current art are probe positioning on the finger and skin pigmentation. In almost 100% of the cases where the current art is used, the caregiver must apply the probe and reposition the probe to obtain enough signal to allow the system to calibrate and operate. This method is time-consuming and costly. It is also well-known that the current art does not work well on individuals with highly pigmented skin.

In many cases the probe portions of the pulse oximeters of current clinical practice are designed to be disposable. For such pulse oximeters the probe contains both the red and infrared light sources and the photodetector. The photodetector is usually a silicon photodiode. Because the probe portion is thrown away after it is used, its cost must be kept as low as possible to provide for practicality and cost effectiveness. However, the need to dispose of the light sources with the probe makes it difficult to reduce cost beyond a certain point. In particular, if the light sources are LEDs (which are not particularly expensive in their own right) they must be checked and handled individually. This is due to the fact that in large scale manufacturing of the LEDs it is difficult to assure that the operating wavelength of an LED remains sufficiently constant to avoid causing error in the frequency-dependent pulse oximetry measurement. One method for dealing with this problem, common in the present art, is to sort the LEDs after manufacturing and then encode each probe in such a manner that the pulse oximetry unit can correct for this wavelength variation. This individual handling of the probe requires effort that adds to the cost of manufacturing the probe.

It is possible to make a pulse oximeter where the light sources are not placed directly on the end of the probe but are instead placed remotely on the end of a fiber optic cable. By itself, this technique does not address the cost effectiveness of disposable probes since the fiber optic cable is not normally designed to be disposable. Disposable probes would generally be prohibitively expensive. However, this problem can be solved by incorporating a small disposable portion of fiber optic cable onto the end of the main fiber optic cable via a simplified coupling connector.

The use of this small disposable portion is greatly facilitated by using lasers as the light source in the oximeter because it is possible to provide for an efficient transfer of light from the light source to a fiber optic cable and from one fiber to another fiber optic cable when lasers are used. In the present patent there are described two basic categories of probe designs: 1) probes which are purely fiber optic in nature, and 2) probes which are a hybrid of fiber optic and conventional electronics. Both categories of designs have significant cost and performance benefits over current practice.

SUMMARY OF THE INVENTION

According to one aspect, the invention is an apparatus for transmitting electromagnetic energy through a portion of a living body. The apparatus comprises first and second sources of electromagnetic energy, a first conduit and a detector. The first source produces electromagnetic energy having a first frequency and the second source produces electromagnetic energy having a second frequency. The first conduit transmits the electromagnetic energies having the first and second frequencies from the first and second sources to the vicinity of the portion of the living body. Light from the first conduit is directed into the body. After transiting the portion of the body the light of both frequencies is then received for analysis. The detector converts the electromagnetic energies to corresponding first and second electrical signals after the transmitted electromagnetic energies have passed through the portion of the living body. The detector may be either a sensor located in the vicinity of the body, or another fiber optic cable (a second conduit). When a second conduit is used the detector may be located remotely from the portion of the body.

In accordance with a second aspect, the invention is a method for transmitting electromagnetic energy through a portion of a living body, the method comprising the steps of: a) providing a source of electromagnetic energy having a first frequency, b) providing a source of electromagnetic energy having a second frequency, c) providing a first conduit to transmit the electromagnetic energies from the sources to the vicinity of the portion of the living body and connecting the first conduit to the sources, d) providing a second conduit to receive the transmitted light, e) providing a detector for analyzing the signal. Portions of the first and second conduits may be detachable, in which case an optical coupler is used at the detached point.

According to another aspect, the invention is a probe for transmitting electromagnetic energy through a portion of a living body and receiving a signal indicative of a parameter affecting the transmission of the electromagnetic energy through the portion of the living body. The electromagnetic energy has a first characteristic wavelength. The probe comprises a connector, a first optical conduit, a first optical element, a second optical element, and a second optical conduit. The connector receives the electromagnetic energy from a source of electromagnetic energy and to receive the information concerning the parameter. The first optical conduit is connected to the connector to transmit the electromagnetic energy away from the connector. The first optical element is connected to the first optical conduit to direct the electromagnetic energy through the portion of the living body. The second optical element receives the electromagnetic energy after it has transmitted through the living body. The received electromagnetic energy carries information concerning the parameter affecting the transmission of the electromagnetic energy through the portion of the living body. The second conduit is connected to the second optical element and to the connector to transmit the information to the connector.

BRIEF DESCRIPTION OF THE DRAWINGS

FIG. 5b is a cross-sectional view of the probe of FIG. 5a.

DETAILED DESCRIPTION OF THE PREFERRED EMBODIMENT OF THE INVENTION

Figure 1:
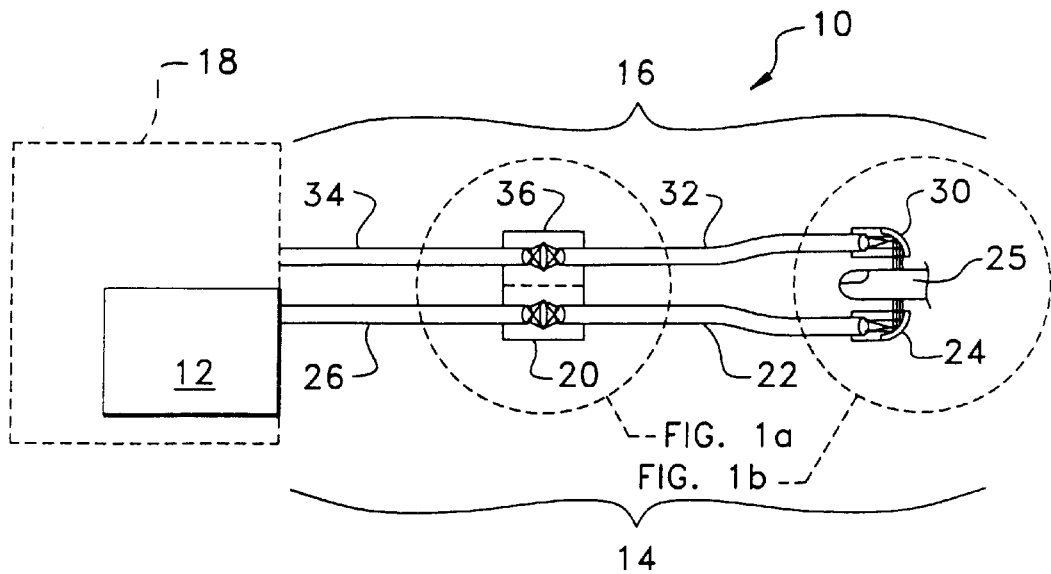
FIG. 1 is a schematic diagram of a preferred embodiment of the apparatus of the invention.

The present invention addresses all of the problems listed above for the current art. FIG. 1 is a schematic diagram of a preferred embodiment of the apparatus of the invention. The apparatus 10 includes a light source 12, a first conduit 14, and a second conduit 16 (which in its totality is the detector portion of the apparatus 10). In the preferred embodiment of the invention, the light source 12 includes a pair of standard (non-customized) diode lasers respective serving as first and second sources of electromagnetic energies. One electromagnetic energy has a frequency corresponding to red light and the other electromagnetic energy has a frequency corresponding to infrared light. These diode lasers are not in contact with the patient. Instead the diode lasers deliver the light through the first conduit 14, which consists of one or more fiber optical cables. These cables may be composed of either a single fiber or a bundle of fibers. The light from the lasers is introduced to the first conduit 14 by means of a conventional beam splitter, such as a dichroic beam splitter. The dichroic beam splitter allows the laser light from one of the diode lasers to pass along a straight-line path into the first conduit 14 and causes the laser light from the other of the diode lasers to be reflected from another direction (say, 90 degrees from the straight-line path of the light from the first diode laser) into the first conduit 14.

If the cables are of the conventional type, composed of a bundle of optical fibers (typically ranging from several fibers to a thousand fibers), as will be described subsequently, efficient coupling of laser light energy can be accomplished through the use of imaging lenses at the ends of the optical fiber bundle. The lenses should provide a 1:1 imaging of the image presented to the end of the bundle. In the case where two optical fiber bundles are placed end-to-end, the desired 1:1 imaging can be accomplished by indexing (or "clocking") means which cause each of the fibers in one bundle to be substantially aligned with responding fibers in the other bundle. In addition, the lens can be used to slightly defocus the image it receives from one optical fiber bundle before transmittal to the other optical fiber bundle in order to keep the transfer of laser light energy efficient.

In the preferred embodiment, both diode lasers deliver the light through a single optical fiber cable (which may have many conductors). The frequency of the laser light is tightly controlled during manufacturing so that no additional tuning of the light is required. In addition, unlike the practice with the current art, the laser light source in the inventive system is not discarded after each use. Instead the laser light source 12 resides with a measurement instrument 18. The measurement instrument 18 can be either a unit known in the conventional current art or a special unit designed to interpret electrical signals produced by the second conduit 16.

The technique of fiber delivery that is part of this inventive system, if combined with LEDs instead of lasers, eliminates the requirement for customization used in the current art.

In addition, the inventive method of delivery reduces the "motion artifact" since both wavelengths of light come from the same physical location (the fiber bundle). The reduction of motion artifact reduces, if not totally eliminates, false alarms, thereby increasing the safety of the system. In order to allow the operator the ability to discard the portion of the measurement system which comes into contact with the patient (required due to sterilization concerns), the first conduit 14 of the inventive system uses a coupler 20 and short length 22 of fiber cable in the portion which terminates in an optical element 24 which contacts a portion 25 (such as a finger) of the patient. The first conduit 14 also includes a main fiber cable 26, which is connected to the source 12 (including the lasers) and coupled to the short length 22 of fiber cable using a plastic connector 28 which contains optics designed to efficiently image the light from the main fiber cable 26 into the short length 22 of fiber cable. This short length 22 of fiber cable is inexpensive and keeps the cost of the discarded portion of the system to a minimum (much less than the cost of the current art, where the customized light sources themselves are discarded). The two wavelengths of light come from the same physical location (the short length 22 of fiber cable and the optical element 24). The inventive method of delivery reduces the "motion artifact" since both wavelengths come from the same physical location; i.e., a single optical fiber cable. The invention eliminates the need for equipment calibration and costly software.

Figure 1A:
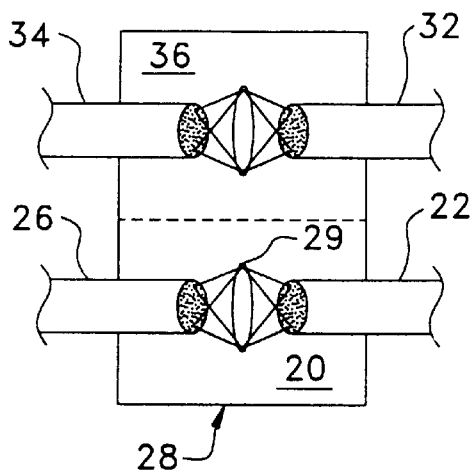
FIG. 1a is a schematic diagram of a preferred embodiment of the fiber optic cable coupler of the invention.

FIG. 1a is a schematic diagram of a preferred embodiment of the fiber optic cable coupler 20 of the invention. The plastic connector 28 includes the fiber optic coupler 20 (and possibly also a fiber optic coupler 36—described subsequently). The preferred embodiment of the fiber optic cable coupler 20 is intended to receive fiber cables 22 and 26 which are multifiber optical cables. The multifiber optical cables allow for inexpensive coupling between the fiber cables 22 and 26 which also features a large signal-gathering area which allows a good signal-to-noise ratio to be maintained.

The multifiber optical cables are indexed relative to the coupler 20 so as to maximize the transfer of light energy from the fiber cable 26 to the fiber cable 22 by aligning the fibers within the fiber cables 22 and 26. The rotational alignment of the fiber cables 22 and 26 is accomplished by the indexing.

The coupler 20 includes a conventional imaging lens 29 which provides 1:1 imaging of the end of the fiber cable 26 onto the end of the fiber cable 22. Although this arrangement will work when the fiber cables 22 and 26 and the lens 29 are spaced so that an exactly focused image of the end of the fiber cable 22 is formed on the end of the fiber cable 26, it can be advantageous to adjust the spacing of these components to provide a slight defocus of the image of the end of the fiber cable 22 on the end of the fiber cable 26. This allows for small misalignments of the components introduced during manufacturing.

The use of remotely mounted lasers allows for the use of extremely bright sources (including remote LEDs) compared to the current art. Laser sources have a very narrow wavelength which allows effective discrimination of the signal from room lights through the use of narrow band optical filters. As shown in FIG. 1, the short length 22 of fiber cable delivers only light to the patient; the excess heat due to the inherent inefficiency of all light sources is dissipated at the other end of the short length 22 of fiber cable from the patient. This arrangement eliminates any chance of burning the patient with waste heat.

The second conduit 16 may have either of two configurations. In one configuration the second conduit 16 includes an optical element 30 and a short length 32 of optical fiber cable, which is attached to a main cable 34 via a coupler 36 (which may be the same as the coupler 20). The main cable 34 is similar to the main fiber cable 26. In this case the preferred embodiment includes the optical element 30 which is a small plastic light collection optic (reflective and/or refractive) bonded onto the patient end of the short length 32 of fiber optic cable. This optic gathers the transmitted light and focuses it into the fiber bundle. After the coupler 36 is the connector which couples the two fibers in the short length 32 of fiber optic cable to the main fiber 34. The main fiber 34 is a length of non-disposable fiber optic cable. In a second preferred configuration, the disposable portion includes a short length 32 of optic fiber cable, conventional photodetectors (such as photodiodes, photomultiplier tubes, CdS sensors, etc., not shown), and a connector (not shown) which couples the short length 32 of optic fiber cable and a receiver electrical connector to carry electrical signals with the main fiber 34.

Figure 1B:
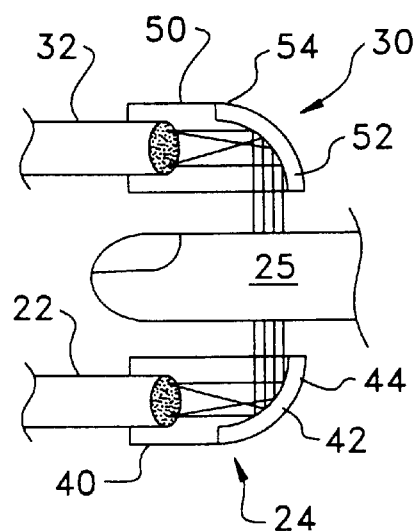
FIG. 1b is a schematic diagram of a preferred embodiment of the optical element of the invention.

FIG. 1b is a schematic diagram of a preferred embodiments of the optical elements 24 and 30 of the invention. Each of the optical elements 24 and 30 are located in close proximity to the portion 25 of the body of the patient. The optical element 24 includes a housing 40 which contains an optical element 42 and means (not shown) for receiving the short length 22 of fiber cable. The optical element 42 receives laser light from the end of the short length 22 of fiber cable and redirects and focuses the laser light into the portion of the body of the patient. The optical element 42 redirects and focuses the laser light by refraction through the body of the optical element 24 (which is preferably made from an inexpensive plastic material), or by reflection from an inexpensive reflective coating 44 on the optical element 24, or by a combination of both.

Similarly, the optical element 30 includes a housing 50 which contains an optical element 52 and means (not shown) for receiving the short length 32 of fiber cable. The optical element 52 receives the laser light that has been transmitted through the portion 25 of the body of the patient and redirects and focuses the laser light onto the end of the short length 32 of fiber cable. The optical element 52 redirects and focuses the laser light by refraction through the body of the optical element 30 (which is also preferably made from an inexpensive plastic material), or by reflection from an inexpensive reflective coating 54 on the optical element 30, or by a combination of both.

The optical element 24 is held in close proximity to the portion 25 of the body of the patient in order to minimize the leakage of light around the portion 25 of the body of the patient, so that the system 10 responds only to laser light which has passed through the portion 25 of the body of the patient.

The methods of redirecting the laser light (as described above) are well-known by those skilled in the art of optical element design. However, in this application, these methods dramatically improve the efficiency of the measurement and reduce artifacts by limiting the field of view of the sensor 10 to the portion 25 of the body of the patient.

In a particular embodiment the lasers and detectors are matched to an interface circuit in the pulse oximetry system. This circuit mimics the behavior of current sensor technologies. In this manner existing pulse oximetry systems may be used in conjunction with this new sensor technology.

The present invention removes the current art requirement of matching or binning of components. This in turn results in a simple software program, eliminating the need for calibration and look-up tables and reduced cost of the disposable portion of the probe. In addition the use of lasers allows for significant enhancement of signal-to-noise levels, while eliminating the problem of waste heat being dissipated on the patient's skin.

Another advantage the present invention provides over the current art is the elimination of an extraneous electrical pathway to ground. Due to the inherent nature of the inventive system the antenna effect of the connector cable is eliminated, enhancing the signal-to-noise ratio. Moreover, the natural properties of the plastic cable provide a high degree of insulation and isolation to any stray electrical currents.

In today's hospital environment two of the biggest concerns are cost containment and cross contamination of infectious disease. The present invention provides for a true disposable device reduced in cost of manufacturing when compared with ordinary current art disposable sensors. At the same time performance is enhanced compared to the current art.

In addition to the advances in noise reduction and the reduction of motion artifact, the present invention reduces the current problem of inaccurate saturation readings due to skin pigmentation. The current art is susceptible to erroneous readings caused by low signal levels induced by the excessive light absorption properties of certain skin pigmentations.

The problem of erroneous readings is currently inadequately addressed by using high intensity LEDs. This results in an increased safety risk due to the potential for burns, especially in the neonatal, infant and pediatric populations. The new art obviates this problem by supplying greater amounts of light (and no waste heat) from the remote source. The system is also inherently immune to extraneous light interference, which reduces false alarms.

Because of the use of a laser light source, the typical difficult cases; i.e. poor perfusion, highly pigmented skin and specific diseases states are eliminated and pose no particular challenge to the new system.

The main instrument portion of this invention is composed of the transmitting lasers, receiving detectors (or electronics), and an electronics package as described above. The main instrument portion is designed to allow the apparatus to emulate the signals from the current art. This is advantageous, since users switching to the present inventive method and apparatus do not need to replace the main instrument apparatus they now use. This saves expenses in both purchasing equipment and retraining users.

According to one aspect this invention is a series of specific designs which make the use of disposable fiber optic pulse oximetry probes practical and inexpensive. There are three primary preferred embodiments which are described in detail in the following. Each of these designs is intended to work in concert with the conventional fiber optic laser pulse oximeter described previously. The designs are illustrated in FIGS. 2, 3 and 4.

Figure 2A:
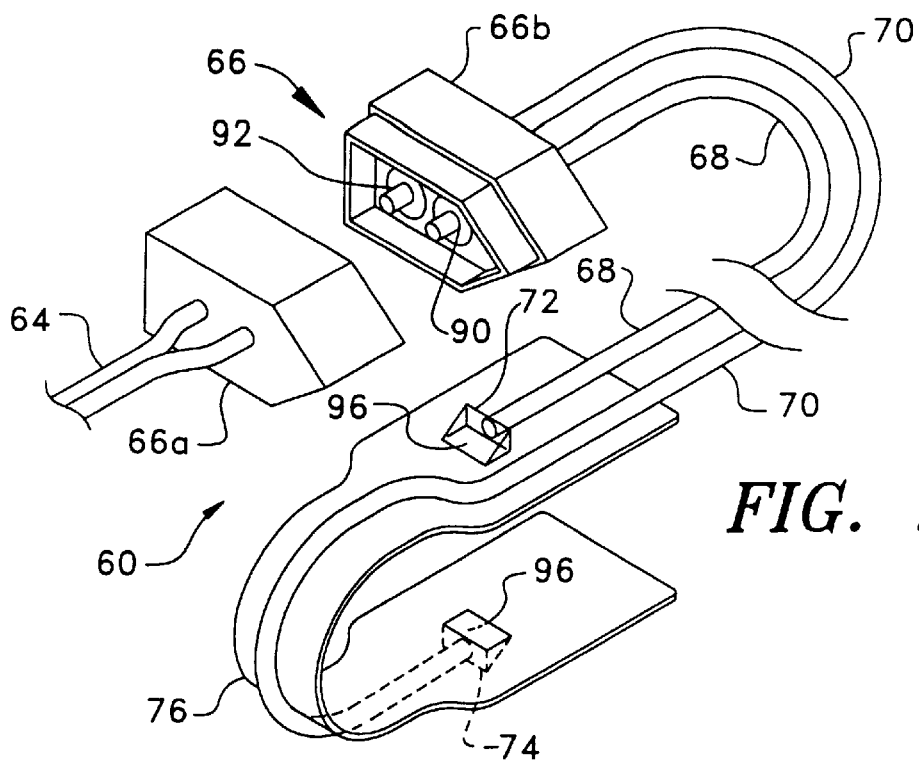
FIG. 2a is a schematic diagram of a first preferred embodiment of a pulse oximetry probe in accordance with the present invention.
Figure 2C:
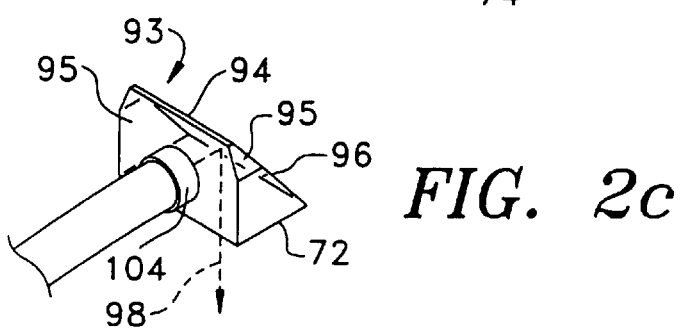
FIG. 2c is a close-up view of a second embodiment of an end optic for use with the present inventive probe.
Figure 2B:
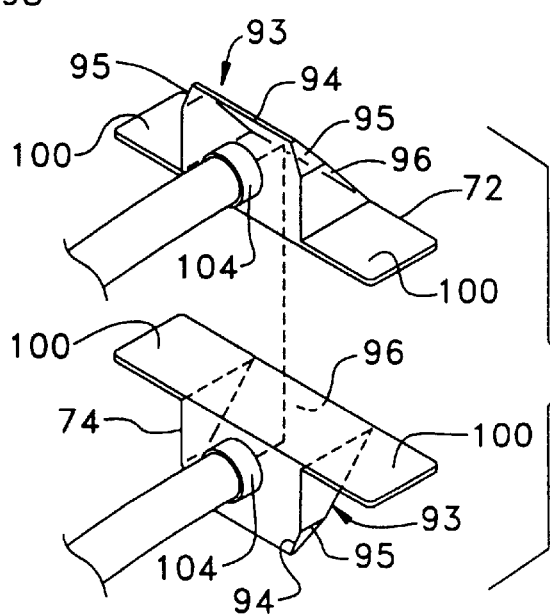
FIG. 2b is a close-up view of a first embodiment of a pair of end optics for use with the present inventive probe.

FIG. 2a is a schematic diagram of a first preferred embodiment of a pulse oximetry probe in accordance with the present invention. The primary design consists of a probe with two separate fiber optic pathways. These pathways may be either a single fiber, or a collection of fibers within a single protective conduit. Such a collection of fibers is often referred to as a fiber bundle. FIG. 2b is a close-up view of a first embodiment of a pair of end optics for use with the present inventive probe. FIG. 2c is a close-up view of a second embodiment of an end optic for use with the present inventive probe.

The probe 60 of FIGS. 2a–c is composed of several functional subgroups which together form a detachable probe capable of transmitting laser light to a finger 25 (or other body portion), projecting the light through the finger 25, receiving the transmitted light, and returning the received light to the permanent fiber bundle 64. These functional subgroups are a connector body 66 (including the mating connector bodies 66a and 66b), fiber optics 68 and 70 which transmit and receive the light, the end optics 72 and 74 which project and collect the light and the substrate 76 which holds the end optics 72, 74 and their respective attached fiber optics 68 and 70 in contact with the patient.

The connector 66 is itself composed of a number of components. In particular there are the mating connector bodies 66a and 66b which are shaped in such a way as to be keyed for a single orientation. This prevents an operator from misconnecting the probe 60 to the permanent fiber cable 64. Typically the body of the connector will be made from Nylon or other hard stable plastic. The two fiber optics 68 and 70 are embedded within the connector body 66b. Each one of these fiber optics 68 and 70 is surrounded by a tapered ferrule 90, 92 which in the connector body 66b (and similarly in the connector body 66a). The ferrules 90 and 92 are used to ensure that the corresponding optics 68 and 70 will be properly aligned when the connector body 66b is attached to the permanent fiber cable 86 by mating with the connector body 66a. Typically these ferrules 90, 92 are made from a very stable material such as metal or polycarbonate plastic while it is possible that the connector body 66 can be made from a more pliable material. The fiber optics 68 and 70 themselves, which may be either single fibers or groups of fibers known as a fiber bundle, then carry the light from the connector body 66a to and from the connector body 66b. One of these fiber optic cables is designed to carry all of the outgoing laser frequencies (typically two frequencies but could be several frequencies).

Typically the fiber optics 68 and 70 are about one foot in length and terminate at the end optics 72 and 74. Both of the end optics 72 and 74 are of similar design and have the general appearance of a prism 93 (typically on the order of a few millimeters). At a minimum this end optic is designed to turn the laser light emitted from the end of the fiber so that it impinges on the patient's finger (or other site) in a nearly perpendicular direction. In addition by curving the angled surface of the end optic it is possible to focus the beam more tightly into the patient to increase the incident intensity, or to restrict the area of illumination. Generally the upper edges 94 of the end optics 72 and 74 will be trimmed as shown in FIGS. 2b and 2c. In addition, as also shown in FIGS. 2b and 2c, the angled surfaces 96 of the optics 72 and 74 can have a curvature to it to focus a beam 98 into the patient, or to collect the light more efficiently in the case of the receiving end optic 74.

Light emitted from the fiber and end optic combination then transits the finger or other body part where the two different frequencies are differentially absorbed by the hemoglobin in the blood. Light scattered from the body is then incident on a similar end optic (which may be different in size and optical power but much the same in appearance). This optic collects the scattered light and then couples it into the second fiber optic, which is usually a fiber bundle. The collected light then travels down the second fiber optic to the connector. In the connector the second fiber optic is encased in a ridged collet to assure proper location within the connector. In the connector this light is transferred, usually via an imaging lens as disclosed previously, to the main fiber optic cable where the light is carried to the receiver. As can be seen, in this design there are no electronic components within the disposable (detachable) probe.

The end optics 72 and 74 may have additional modifications. One such modification is the inclusion of a small set of extensions, or feet 100, whose purpose is to ensure the proper orientation of the end optics 72 and 74 relative to the substrate 76 to which the end optics 72 and 74 are attached. When the substrate 76 is wrapped around the patient's finger, the end optics 72 and 74 with their feet 100 will be pressed against the patient's finger. Accordingly, the broader stance of the feet 100 will assure proper orientation of the end optics 72 and 74.

Another such modification of the end optics 72 and 74 is the inclusion of a semi-spherical (or nearly spherical) optic 104 at the end of the fiber optics 72 and 74 immediately prior to the prism portion 93. The same result may be obtained by spherically polishing the end of the fiber optics 72 and 74 in the case of a single fiber. This has the effect of collimating, or slightly focusing, the light emitted by the fiber optics 72 and 74.

This emitting light is generally in the form of a rapidly expanding cone, and by collimating it the efficiency of the prism portions of the end optics 72 and 74 are greatly improved. Similar modifications may be made to the receiver end optic 74. The receiver end optic 74 is connected to the return fiber optic 70 which may be either a single fiber or a fiber bundle. In addition this fiber optic 70 may be made of glass or plastic. In the case of a plastic fiber optic it is possible to form a permanent bend or set into the fiber optic 70 during manufacturing through the application of heat and pressure. It is possible to incorporate such a set into the return fiber in the area where it and the substrate wrap around the tip of the finger. This would assist in the proper placement of the probe on the finger.

Figure 3A:
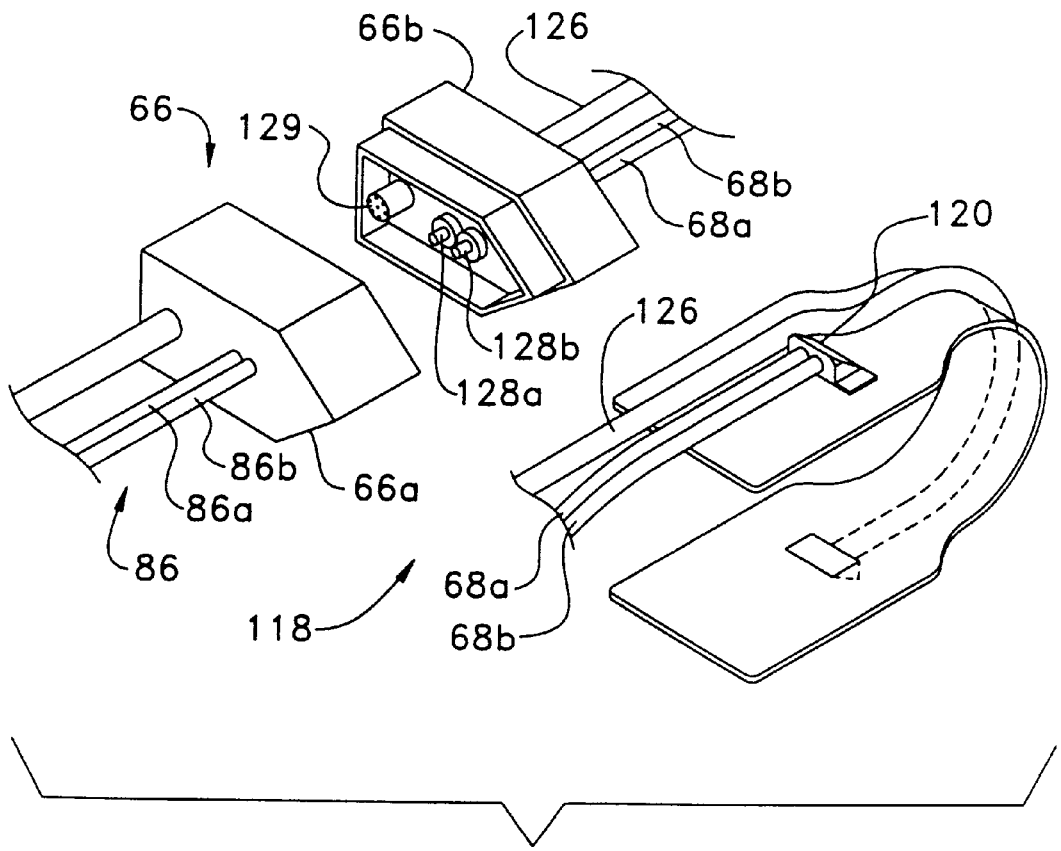
FIG. 3a is a schematic diagram of a second preferred embodiment of a pulse oximetry probe in accordance with the present invention.
Figure 3B:
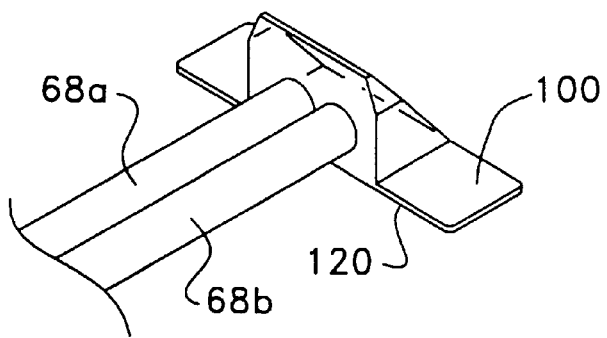
FIG. 3b is a close-up view of a third embodiment of an end optic for use with the present inventive probe.
Figure 4:
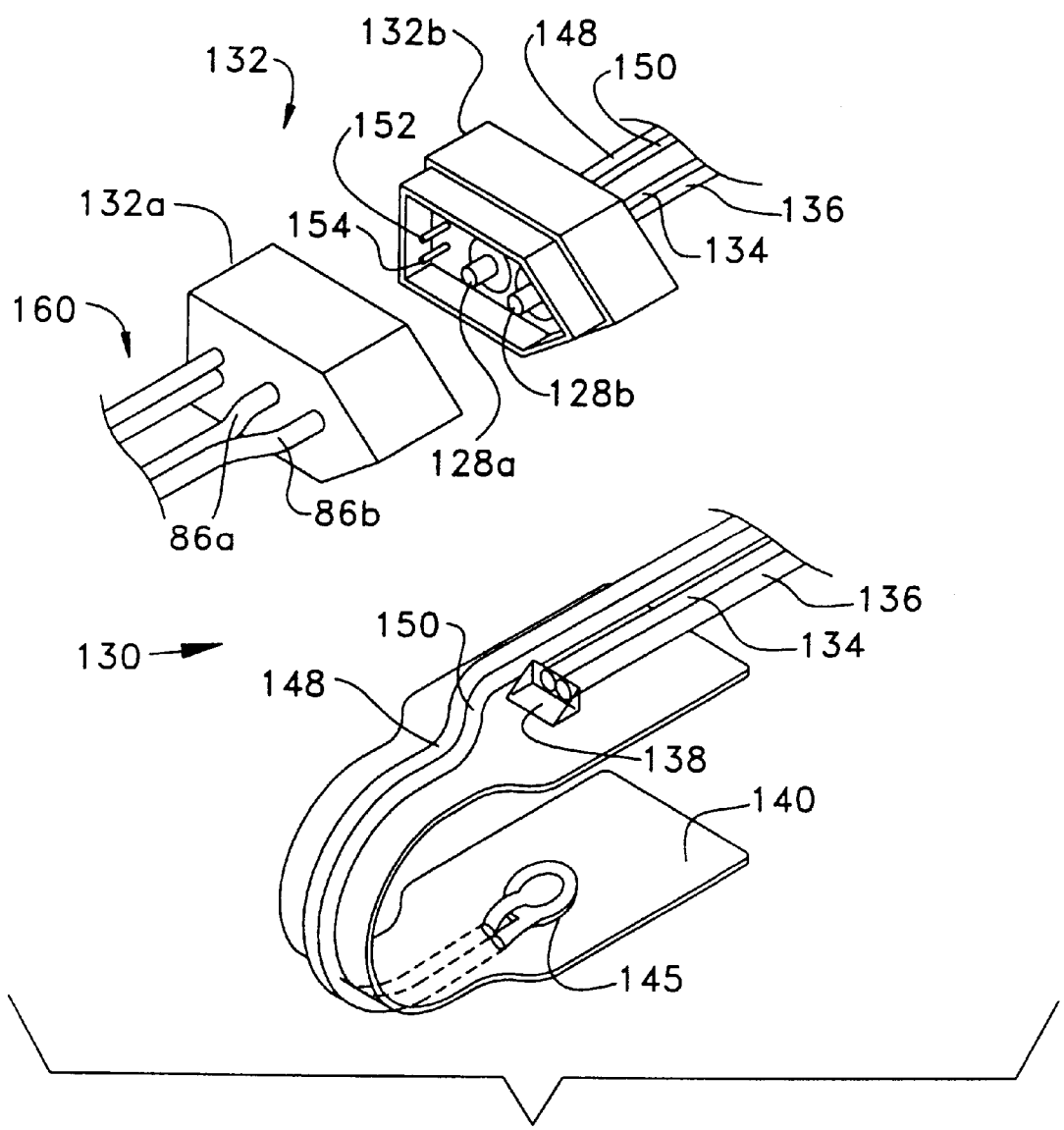
FIG. 4 is a schematic diagram of a third preferred embodiment of a pulse oximetry probe in accordance with the present invention.

FIG. 3a is a schematic diagram of a second preferred embodiment of a pulse oximetry probe in accordance with the present invention. This design of the probe 118 is similar to the design of FIGS. 2a–c with some significant changes. This design has a keyed connector similar to the connector 66 shown in FIGS. 2a–c, but in this case there are two distinct fiber optics 68a and 68b which are used to deliver light to the patient. One fiber optic 68a is for the red light and the other fiber optic 68b is for the infrared light. This separation of the fiber optic 68 is reflected in the permanent fiber optic cable 86 which also has two distinct fibers (86a and 86b) for the transmitted light. By this means it is possible to take advantage of a manufacturing process known as pigtailing by which the laser diodes at the transmitter portion of the permanent cable 86 are pigtailed to the transmitting fiber optic cable. This assures the proper and stable alignment of the laser diodes to the transmitting fiber optic cable. On the disposable probe these two fibers terminate in a single end optic 120 which is similar to the end optic 72 described in the first design. FIG. 3b is a close-up view of a third embodiment of an end optic for use with the present inventive probe. As in the first design and FIG. 3b, the end optic 120 may be modified with spherical lenses and feet-like extensions to improve its overall performance. The return pathway is identical to that disclosed in the preceding design and shown in FIGS. 2a–c. In FIG. 3a the return fiber optic cable 126 is specifically shown to be a fiber bundle but it could also be a single fiber.

In this case there are two fiber cables 68a and 68b that are used to conduct the two different laser frequencies, one for each frequency. This has the advantage of allowing the lasers to be coupled as individuals using the "pigtailing" process discussed previously. This technique is of interest due to the potential savings which the use of pigtailing may provide during manufacturing of the main fiber optic cable and the oximeter box. All other aspects of the second preferred embodiment of the probe 118 are similar to the first preferred embodiment.

In FIG. 3a the connector shows three distinct fiber optic ends. The two ends 128a and 128b on the right are the input fibers for the two different frequencies, while the fiber optic 129 on the left is the fiber bundle which returns the transmitted light from the patient. The two fiber optics 68a and 68b which bring the laser light to the patient both terminate in the same end optic 120 and are closely spaced within the optic 120. This is important to ensure the highest possible level of common light paths to reduce any erroneous information caused by probe motion. In both of the first two probe designs (shown in detail in FIGS. 2a–c and 3a–b) the returning fiber optic bundle may be thermoformed so that it takes a permanent "set" or form to assist in the application of the probe to the finger.

FIG. 4 is a schematic diagram of a third preferred embodiment of a pulse oximetry probe in accordance with the present invention. The third preferred embodiment is a hybrid design which uses a combination of fiber optics and conventional electronic components to provide for the oximetry measurement. In this design the optical configuration is simplified while retaining much of the benefit of the fully fiber optic design since much of the cost is in the selection and calibration of the light sources whereas the photodiode is inexpensive. The third preferred embodiment of the probe 130 is a significant departure from the preceding two in that it is not an entirely fiber optic design. This third probe design takes advantage of the fact that most of the cost-savings available in a disposable fiber optic design comes from not having to dispose of the light sources which must be calibrated individually, while making a smaller departure from existing technology by keeping the on-site photodetector of the prior art. In this case the light still originates from laser diodes located at the instrument end of the permanent cable 131. The light from the laser diodes is delivered to a keyed connector set 132 (and including mating connector bodies 132a and 132b), similarly to the designs of FIGS. 2 and 3.

Specifically, in FIG. 4 the delivered light is shown to come through a set of two fiber optics 134, 136 as in the second design. However, a single fiber optic 134 as in the first preferred embodiment of the probe design may just as well be used. The transmitting fiber optics 134 and 136 terminate in an end optic 138 of the type described in the first and second probe designs. The receiving side of the substrate 140 contains a photodetector 145 such as a standard photodiode of the type used in the current art. The transmitted light signals are converted to electrical signals at the photodetector 145 and transmitted to the connector 132 on conducting wires 148, 150 where it terminates in two electrical pins 152 and 154. These pins 152 and 154 mate with electrical terminations in the connector 132 on the permanent cable 160 for transmission back to the instrument.

Figure 5A:
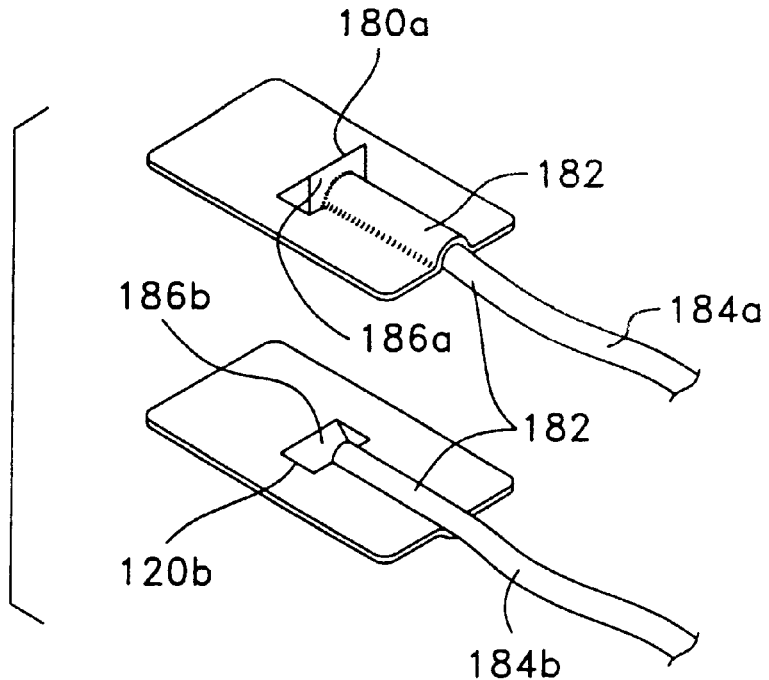
FIG. 5a is a schematic diagram of a fourth preferred embodiment of a pulse oximetry probe in accordance with the present invention.
Figure 5B:
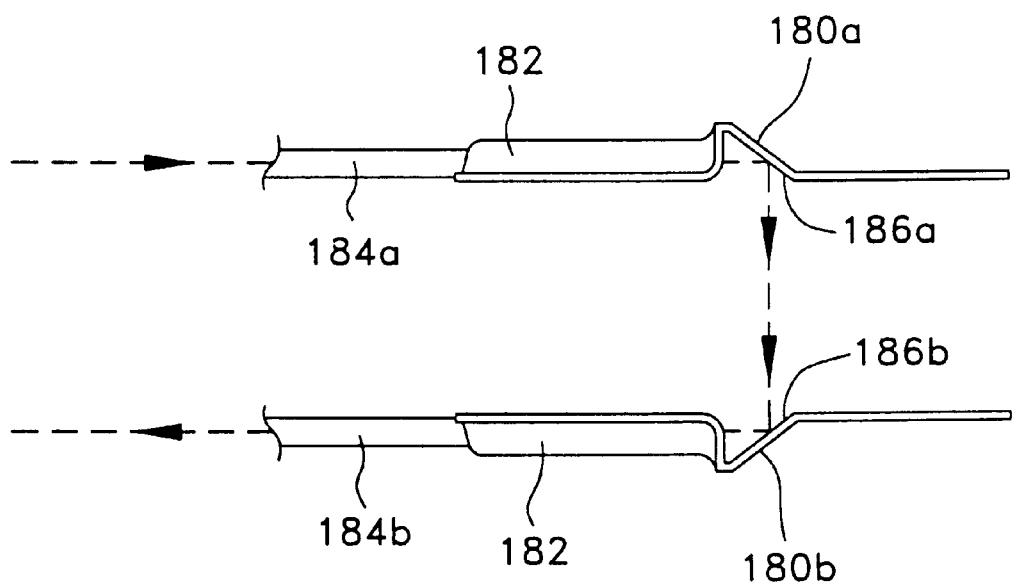

FIG. 5a is a schematic diagram of a fourth preferred embodiment of a pulse oximetry probe in accordance with the present invention. FIG. 5b is a cross-sectional view of the probe of FIG. 5a. FIGS. 5a–b show an alternative method for providing end optics 180a and 180b for both the transmission and receiving fiber optic or fiber optic bundles. In this case, either of the end optics 180 is formed in plastic or plastic-like material by any of the standard manufacturing methods. Thermoforming and injection molding are specific examples but other methods will be commonly known to those skilled in the relevant arts. The end optic 180 has a small trough 182 (or other receiver) designed to accept the fiber 184 (or fiber bundle). The trough 182 is designed to ensure proper positioning of the fiber 184 (or fiber bundle) relative to an angled surface 186. The purpose of the angled surface 186a is to redirect the light emitted from the fiber 184a. Typically the angled surfaces 186a and 186b will be at 45 degrees to both the fibers 184a and 184b and the skin of the patient. The angled surfaces 186a and 186b may be coated with a reflective coating or a diffusive coating. In addition the angled surfaces 186a and 186b may be curved to impart a focusing to the beam to increase the intensity of the incident light. The receiving optic 180b is similar in appearance and construction to the transmitting optic 180a. The receiving optic 180b may also be curved in shape to improve the collection efficiency.

In this case the optics 180a and 180b provide the same function as the optics 72, 74, 120 and 138, but they are designed to be easy to manufacture via thermoforming or injection molding which could be advantageous from the standpoint of manufacturing cost. In this design the optics 180a and 180b are formed by shaping a piece of plastic to the proper shape as shown. In particular the cast or molded shape of the optics in FIGS. 5a–b are designed to position the fibers 184a and 184b and to reflect the light emitted by the fiber to change its direction so that it is substantially perpendicular or normal to the surface of the patient. There may be some advantages in terms of spatial signal averaging which are accrued through the use of a diffusive surface at this location.

Figure 6A:
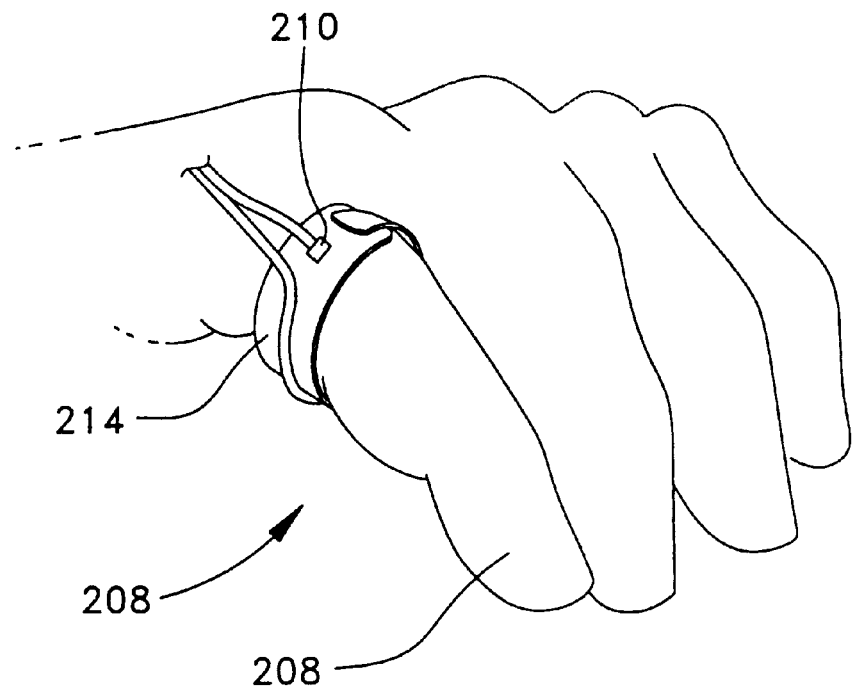
FIG. 6a is a schematic diagram of a fifth preferred embodiment of a pulse oximetry probe in accordance with the present invention.
Figure 6B:
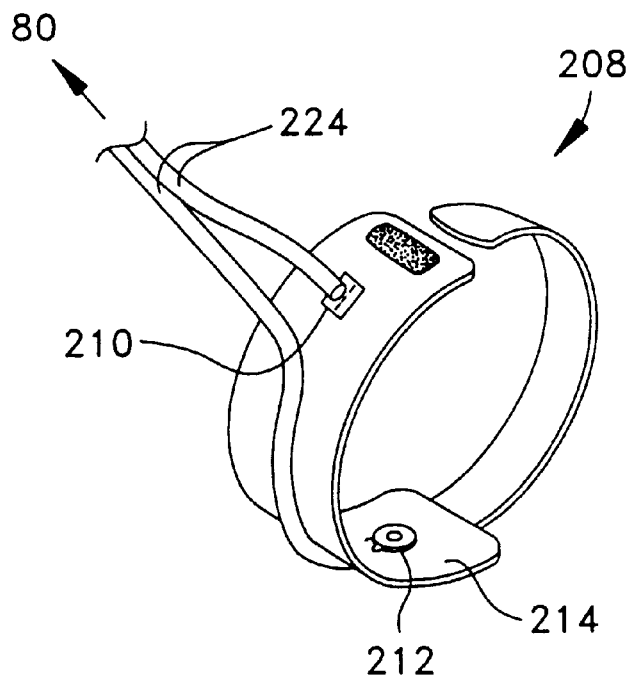
FIG. 6b is a perspective view of the fifth preferred embodiment of a pulse oximetry probe in accordance with the present invention.

In addition to finger tip configurations (measurement of pulse oximetry at the finger tip are the current standard in the art), it is possible to modify the designs shown here for use at the base of a finger 206. FIG. 6a is a schematic diagram of a fifth preferred embodiment of a pulse oximetry probe in accordance with the present invention and FIG. 6b is a perspective view of the fifth preferred embodiment of a pulse oximetry probe in accordance with the present invention. In this preferred embodiment, the sensor configuration has been changed to allow its use at the base of a finger 206 rather than the finger tip. There are some practical advantages to this site since there is less physical motion and the practitioner need not worry about site anomalies such as fingernail polish which may reduce the efficacy of the sensor. To effectively use this site the probe must be changed in configuration. In this case the transmission optic 210 is not placed diametrically opposite to the receiver optic 212. The receiver optic 212 is shown as a photodiode, but may be a fiber optic cable with an end optic as discussed above. These transmitting and receiving elements 210 and 212 are placed on an adhesive pad substrate 214 which wraps around the base of the finger 206.

In this manner, incident light which is emitted from the transmitting end optic 210 impinges on the body and is reflected back out to be received by the receiving end optic 212 from which it is conducted back to the connector 80 via a fiber optic conduction leg 224. The use of fiber optics and end optics in the reflecting geometry is advantageous since the limited fields of view of the transmission and receiving paths prevent any stray light that has moved along the surface of the skin from being detected. This light does not typically carry the desired information and is therefore a source of artifacts and noise.

Figure 7:
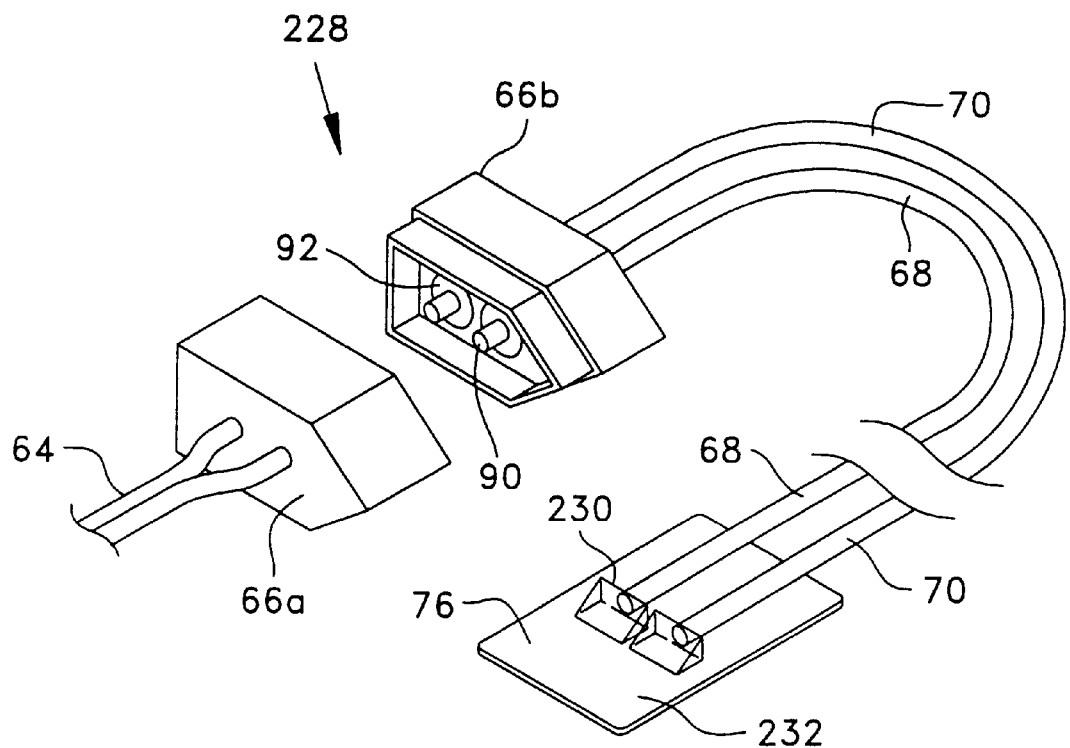
FIG. 7 is a schematic diagram of a sixth preferred embodiment of a pulse oximetry probe in accordance with the present invention.

In this sixth preferred embodiment of the probe 228 shown in FIG. 7, the emitting fiber optic is not diametrically opposed to the sensor or receiving fiber optic combination such as receiving end optic 232. (In FIG. 7, parts that are identical or similar to those shown in FIG. 2 are given the same reference numbers as they have in FIG. 2.) Instead they are slightly closer together. This geometry change is to avoid the bulk of the finger bone which absorbs the light but provides no signal information. This geometry change is facilitated by the use of lasers and fibers in the transmission leg of the device. This is due to the directional nature of the light which is emitter from the fiber/end optic configuration which assures that the measured light in the majority is obtained from within the body rather than transmitted along the surface. By locating the probe 208 in this position using this configuration advantages are gained in that the probe 208 is in an area of reduced motion, and the practitioner need not worry about miscellaneous considerations such as removing fingernail polish, etc.

All of the designs shown can be reconfigured for reflectance pulse oximetry by arranging the emitting end optic and receiving end optic (or photodiode) in a planar fashion.

While the foregoing is a detailed description of the preferred embodiment of the invention, there are many alternative embodiments of the invention that would occur to those skilled in the art and which are within the scope of the present invention. Accordingly, the present invention is to be determined by the following claims.

What is claimed is:

1. A disposable probe for directing first laser light from a laser light source through a portion of a living body and for receiving second laser light that has passed through the portion of the living body, the probe comprising:

a connector adapted to be removably connected to a laser light source to receive the first laser light from the laser light source and adapted to transmit the second laser light that has passed through the portion of the living body to a detector, said connector adapted to be removably connected to the detector;

a first fiber optic cable having a proximal end connected to the connector and a distal end, said first fiber optic cable being adapted to conduct the first laser light to a vicinity of the portion of the living body to be transmitted through the portion of the living body;

a second fiber optic cable having a proximal end connected to the connector and a distal end, said distal end of said second fiber optic cable being adapted to receive the second laser light that has been transmitted through the portion of the living body; and a terminal element comprising:
  a first optical element that receives the first laser light from the distal end of the first fiber optic cable and directs the first laser light onto and through the portion of the living body, and
  a second optical element that receives the second laser light that has passed through the portion of the living body and transmits the second laser light to the distal end of the second fiber optic cable.

2. The probe of claim 1, wherein the connector is keyed to be connected to a source of laser light and to a circuit for processing the information in a unique manner.

3. The probe of claim 1, wherein the first optical element is a prism having a reflective surface.

4. The probe of claim 3, wherein the first optical element receives the laser light in a predetermined direction and includes stability feet located transversely to the predetermined direction.

5. The probe of claim 1, wherein the second optical element is a prism having a reflective surface.

6. The probe of claim 5, wherein the second optical element receives the laser light in a predetermined direction and includes stability feet located transversely to the predetermined direction.

7. The probe of claim 1, wherein the first fiber optic cable is adapted to transmit laser light having a first characteristic wavelength and to transmit laser light having a second characteristic wavelength.

8. The probe of claim 7 wherein the first fiber optic cable includes a single optical fiber.

9. The probe of claim 7 wherein the first fiber optic cable includes an optical cable bundle.

10. The probe of claim 1, wherein the second conduit is a single optical fiber adapted to transmit laser light having a first frequency.

11. The probe of claim 10 wherein the second fiber optic cable includes an optical fiber bundle.

12. The probe of claim 1, wherein the second optical element includes a photodiode transducer that converts the second laser light to an electrical signal carrying information concerning the parameter affecting the transmission of the first laser light through the portion of the living body.

* * * * *